US010925780B2

(12) United States Patent
Stabelfeldt et al.

(10) Patent No.: US 10,925,780 B2
(45) Date of Patent: Feb. 23, 2021

(54) ABSORBENT ARTICLE WITH WIPE GRIPPER HANDLE

(71) Applicant: Kimberly-Clark Worldwide, Inc., Neenah, WI (US)

(72) Inventors: Sara Jane Wille Stabelfeldt, Neenah, WI (US); Nicole Jeane Barna, Neenah, WI (US); Nancy Ellen Dawson, Neenah, WI (US); John T. Hahn, Merrill, WI (US); Eric Donald Johnson, Larsen, WI (US); Paul Alois Weber, Menasha, WI (US); Georgia Lynn Zehner, Larsen, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 1058 days.

(21) Appl. No.: 14/874,526

(22) Filed: Oct. 5, 2015

(65) Prior Publication Data
US 2016/0120710 A1    May 5, 2016

Related U.S. Application Data

(60) Provisional application No. 62/073,386, filed on Oct. 31, 2014.

(51) Int. Cl.
*A61F 13/514* (2006.01)
*A61F 13/84* (2006.01)

(52) U.S. Cl.
CPC ........ *A61F 13/51476* (2013.01); *A61F 13/84* (2013.01); *A61F 2013/51486* (2013.01)

(58) Field of Classification Search
CPC .............. A61F 13/84; A61F 2013/4512; A61F 13/51476; A61F 2013/51486; A61F 13/51456; A61F 2013/51468; A61F 2013/51492; A61F 2013/51494
See application file for complete search history.

(56) References Cited

U.S. PATENT DOCUMENTS

| 3,865,110 A | | 2/1975 | Traverse | |
| 4,051,854 A | * | 10/1977 | Aaron | A41B 13/04 604/394 |
| 5,037,414 A | * | 8/1991 | Booth | A61F 13/551 604/385.13 |

(Continued)

FOREIGN PATENT DOCUMENTS

| EP | 1 688 117 A1 | | 8/2006 | |
| GB | 2298354 | * | 9/1996 | .............. A61F 13/15 |

(Continued)

*Primary Examiner* — Michael M Kidwell
(74) *Attorney, Agent, or Firm* — Kimberly-Clark Worldwide, Inc.

(57) ABSTRACT

An absorbent article includes a front waist region, a rear waist region, and a crotch region, the front waist region having a front fastener and an outermost surface, the absorbent article further including a longitudinal axis and a lateral axis. The absorbent article also includes an absorbent assembly including a bodyside liner, an outer cover, and an absorbent body disposed between the bodyside liner and the outer cover; and a gripper handle disposed in the front waist region and extending from the outermost surface, wherein the outermost surface is one of the outer cover and the front fastener.

9 Claims, 12 Drawing Sheets

(56) References Cited

U.S. PATENT DOCUMENTS

| | | | |
|---|---|---|---|
| 5,308,345 A | 5/1994 | Herrin | |
| 5,593,401 A | 1/1997 | Sosalla et al. | |
| 5,778,110 A | 7/1998 | Furuya | |
| 5,904,675 A | 5/1999 | Laux et al. | |
| 5,938,652 A | 8/1999 | Sauer | |
| 6,102,901 A * | 8/2000 | Lord | A61F 13/5633 604/386 |
| 6,258,076 B1 | 7/2001 | Glaug et al. | |
| 6,264,639 B1 | 7/2001 | Sauer | |
| 6,425,889 B1 | 7/2002 | Kitaoka et al. | |
| 6,485,478 B2 | 11/2002 | Imai et al. | |
| 7,727,211 B2 | 6/2010 | Lavon et al. | |
| 7,867,208 B2 * | 1/2011 | Samuelsson | A61F 13/15756 604/385.13 |
| 7,982,090 B2 | 7/2011 | Snauwaert et al. | |
| 7,993,314 B2 | 8/2011 | Asp et al. | |
| 2001/0037102 A1 | 11/2001 | Sugito | |
| 2003/0109841 A1 | 6/2003 | Edwards | |
| 2005/0137564 A1 | 6/2005 | Strannemalm | |
| 2005/0143710 A1 | 6/2005 | Van Gompel et al. | |
| 2006/0020252 A1 * | 1/2006 | Strong | A61F 13/551 604/385.13 |
| 2006/0111685 A1 | 5/2006 | Kawata et al. | |
| 2006/0241558 A1 * | 10/2006 | Ramshak | A61F 13/493 604/385.09 |
| 2006/0282056 A1 | 12/2006 | McDonald | |
| 2007/0032769 A1 | 2/2007 | Cohen et al. | |
| 2007/0260209 A1 * | 11/2007 | Brilman | A61B 5/1116 604/361 |
| 2008/0051744 A1 | 2/2008 | Cummings | |
| 2008/0262458 A1 * | 10/2008 | Winqvist | A61F 13/495 604/374 |
| 2010/0152695 A1 * | 6/2010 | Stabelfeldt | A61F 13/84 604/385.09 |
| 2011/0034896 A1 | 2/2011 | Bai | |
| 2011/0092939 A1 | 4/2011 | Donoho | |
| 2011/0098668 A1 | 4/2011 | Thorson et al. | |
| 2012/0071850 A1 | 3/2012 | Tomassetti | |

FOREIGN PATENT DOCUMENTS

| | | | | |
|---|---|---|---|---|
| GB | 2 326 811 A | 1/1999 | | |
| GB | 2 389 300 A | 12/2003 | | |
| WO | WO 1998/013002 A1 | 4/1998 | | |
| WO | WO 2012/040296 | * | 3/2012 | A61F 13/15 |

* cited by examiner

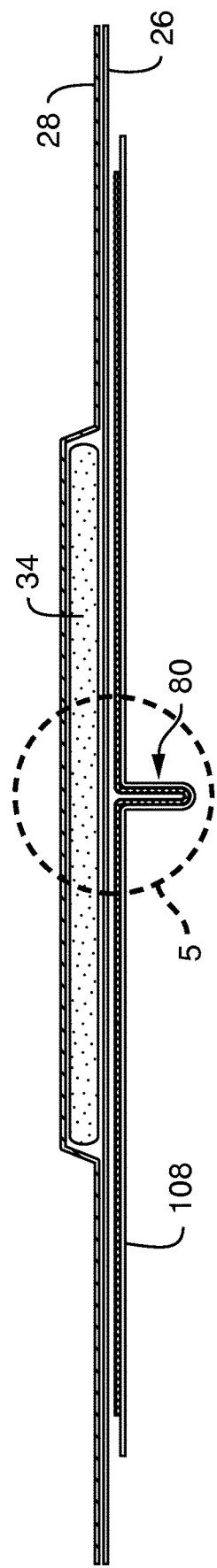
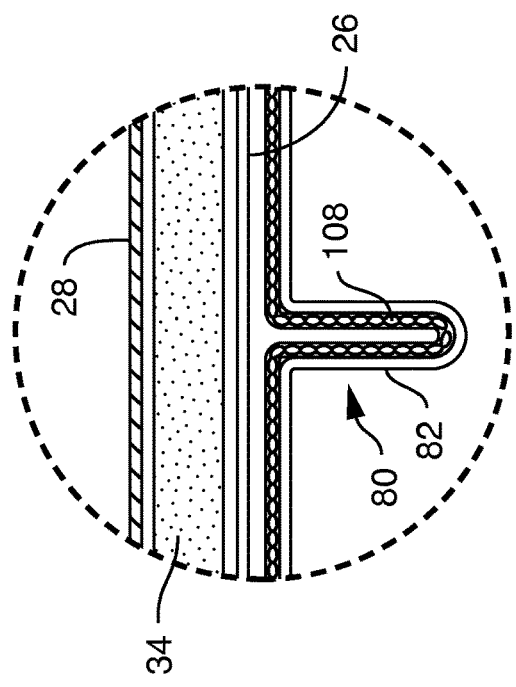
FIG. 4
FIG. 5

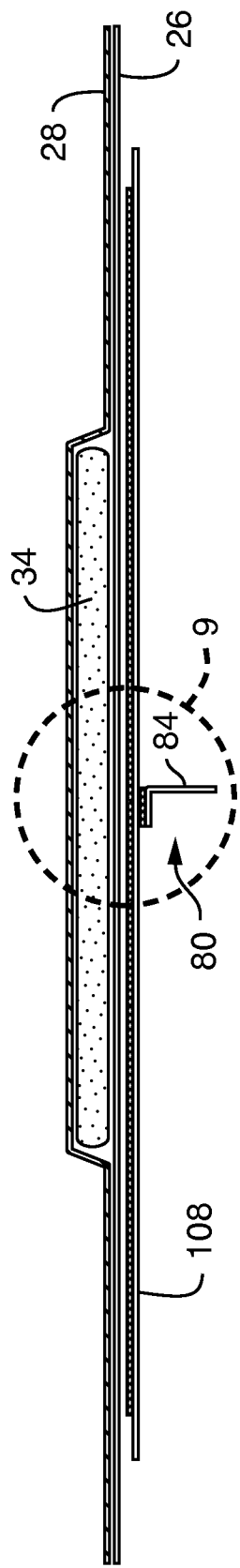
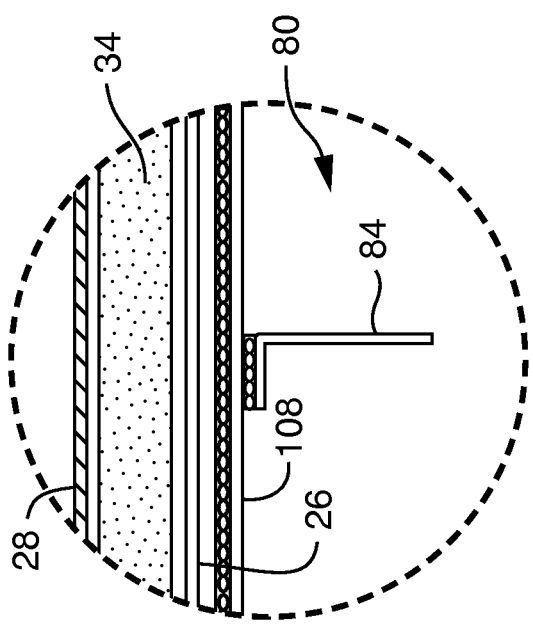

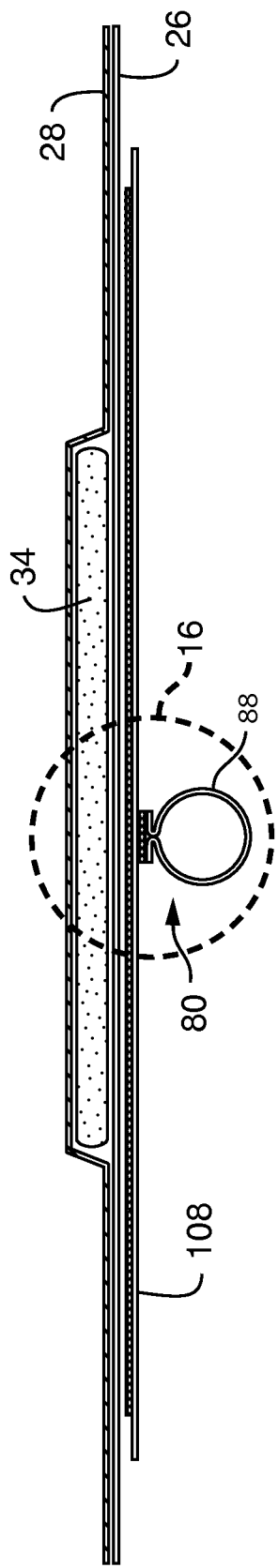
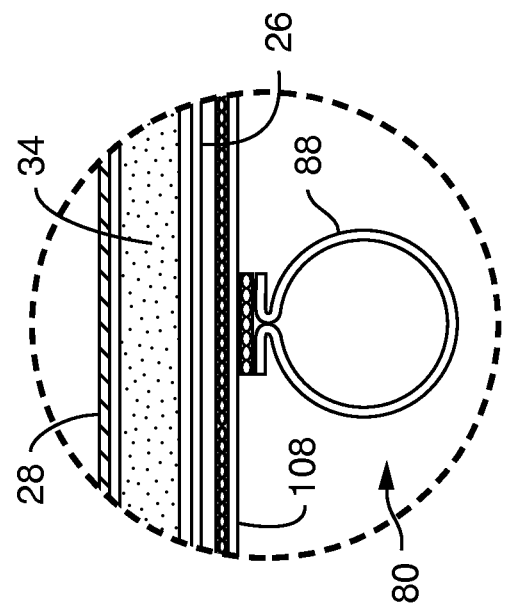

ABSORBENT ARTICLE WITH WIPE GRIPPER HANDLE

RELATED APPLICATIONS

The present application claims priority to U.S. Provisional Application No. 62/073,386, filed Oct. 31, 2014, the contents of which are hereby incorporated by reference in a manner consistent with the present application.

BACKGROUND

The present disclosure relates to absorbent articles. When absorbent articles become soiled with exudates and are changed from the wearer, it is common for the lower abdomen and/or crotch region of the wearer to become soiled by urine, fecal matter, and/or other bodily discharges. Prior to replacing the soiled absorbent article and replacing it with a new, clean absorbent article, the skin of the wearer is cleansed. This cleaning of the skin can be done in a variety of ways and using a variety of different materials, but caregivers commonly use wet wipes or cloths to clean the wearer's skin. In some circumstances, caregivers can choose to use a clean portion of an inner layer of the soiled absorbent article to provide a first wipe to cleanse the wearer's skin in the lower abdomen or crotch region prior to using wet wipes, cloths, or tissues.

To perform this initial wipe, a caregiver can attempt to pinch or gather the front waist region of the absorbent article to obtain a grip on the absorbent article to use the inner layer of the absorbent article in a wiping fashion. However, pinching or gathering the front waist region of the absorbent article can reduce the effective area of the inner layer of the absorbent article that is intended to wipe the wearer's skin in the soiled area as well as create an uneven inner surface of the absorbent article that is not as conducive to wiping as the initial flat surface. Pinching or gathering the front waist region of the absorbent article in this fashion can also expose a caregiver's fingers or hand to the exudates remaining on the wearer's skin, as the gathered material in the front waist region can fold over due to pinching or gathering of the absorbent article near the front waist edge of the absorbent article where the absorbent article can have less structural integrity and/or due to the wiping motion of the caregiver employs with the absorbent article. Additionally, gripping the front waist region of the absorbent article in such a fashion can prove to be difficult altogether as the outer cover materials can have a low coefficient of friction, resulting in the gathered or pinched area of the front waist region slipping out of the caregiver's hands while trying to wipe the soiled area. While some of these issues have been recognized in prior documents, no effective solution has been provided to date to adequately address these issues.

Thus, there remains a need for an absorbent article that can provide improved functionality for the caregiver to utilize the absorbent article as a first wipe to cleanse the wearer's skin. There also remains a need for an absorbent article that protects the caregiver's hands from the wearer's exudates while still providing a proper grip on the absorbent article to utilize the absorbent article in a wiping fashion.

Previous attempts to provide a solution have typically involved providing a hand-sized pocket on the front on the front of the absorbent article, but these solutions can be difficult to manufacture. There is a need for alternate methods of grasping the front portion of the diaper that provides control of the inner wiping surface and protects the hand from contamination while adding a visual cue to the caregiver and at the same time simplifying manufacturing process.

SUMMARY

In one aspect, an absorbent article includes a front waist region, a rear waist region, and a crotch region, the front waist region having a front fastener and an outermost surface, the absorbent article further including a longitudinal axis and a lateral axis. The absorbent article also includes an absorbent assembly including a bodyside liner, an outer cover, and an absorbent body disposed between the bodyside liner and the outer cover; and a gripper handle disposed in the front waist region and extending from the outermost surface, wherein the outermost surface is one of the outer cover and the front fastener.

In another aspect, an absorbent article includes a front waist region, a rear waist region, and a crotch region, the front waist region having a front fastener and an outermost surface, the absorbent article further including a longitudinal axis and a lateral axis. The absorbent article also includes an absorbent assembly including a bodyside liner, an outer cover, and an absorbent body disposed between the bodyside liner and the outer cover; and a gripper handle disposed in the front waist region and extending from the outermost surface, wherein the gripper handle is affixed to the outermost surface, wherein the outermost surface is one of the outer cover and the front fastener, wherein the gripper handle has a handle longitudinal axis, and wherein the handle longitudinal axis is generally parallel to the longitudinal axis of the absorbent article.

In still another aspect, an absorbent article includes a front waist region, a rear waist region, and a crotch region, the front waist region having a front fastener and an outermost surface, the absorbent article further including a longitudinal axis and a lateral axis. The absorbent article also includes an absorbent assembly including a bodyside liner, an outer cover, and an absorbent body disposed between the bodyside liner and the outer cover; and a gripper handle disposed in the front waist region and extending from the outermost surface, wherein the gripper handle is formed as part of the outermost surface, wherein the outermost surface is one of the outer cover and the front fastener, wherein the gripper handle has a handle longitudinal axis, and wherein the handle longitudinal axis is generally parallel to the longitudinal axis of the absorbent article.

BRIEF DESCRIPTION OF DRAWINGS

A full and enabling disclosure thereof, directed to one of ordinary skill in the art, is set forth more particularly in the remainder of the specification, which makes reference to the appended figures in which:

FIG. 4 is a cross-section view of the article of FIG. 3, taken along the 4-4 line of FIG. 3.

FIG. 5 is a close-up cross-section view of the article of FIG. 4.

FIG. 8 is a cross-section view of the article of FIG. 7, taken along the 8-8 line of FIG. 7.

FIG. 9 is a close-up cross-section view of the article of FIG. 8.

FIG. 15 is a cross-section view of the article of FIG. 14, taken along the 15-15 line of FIG. 14.

FIG. 16 is a close-up cross-section view of the article of FIG. 15.

Figure 1:
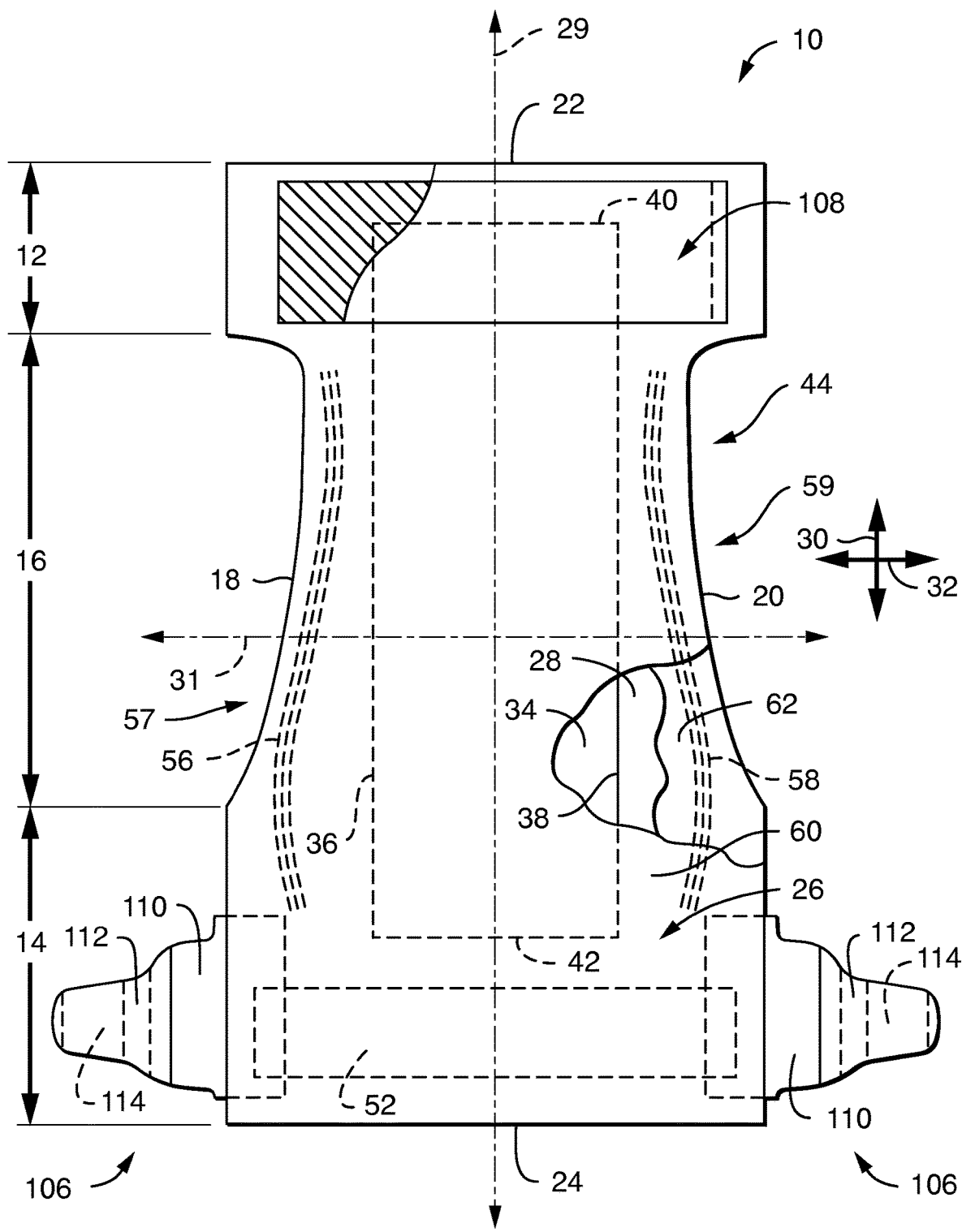
FIG. 1 is a top plan view of an exemplary aspect of an absorbent article, the absorbent article being in a stretched, laid flat configuration, with the outer cover facing the viewer.

Repeat use of reference characters in the present specification and drawings is intended to represent the same or analogous features or elements of the disclosure.

DETAILED DESCRIPTION

In an aspect, the present disclosure is generally directed towards an absorbent article having a gripper handle disposed on the outer surface in the front waist region of the absorbent article. The gripper handle can aid a caregiver with providing an initial cleaning of the wearer after the article is soiled by the wearer and prior to changing the absorbent article. In preferred aspects, the selective location and size of the gripper handle can provide advantages to the caregiver. Each example herein is provided by way of explanation and is not meant as a limitation. For example, features illustrated or described as part of one aspect or figure can be used on another aspect or figure to yield yet another aspect. It is intended that the present disclosure include such modifications and variations.

When introducing elements of the present disclosure or the preferred aspect(s) thereof, the articles "a", "an", "the" and "said" are intended to mean that there are one or more of the elements. The terms "comprising", "including" and "having" are intended to be inclusive and mean that there can be additional elements other than the listed elements. Many modifications and variations of the present disclosure can be made without departing from the spirit and scope thereof. Therefore, the exemplary aspects described above should not be used to limit the scope of the disclosure.

The term "absorbent article" refers herein to an article that can be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers that are then sent to a carding process that separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers can be subject to adhesive processes to bind the fibers together such as by the use of powder adhesives. The carded web can be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films that constitute liquid transfer films, as well as films that do not transfer fluids, such as, but not limited to, barrier films, filled films, breathable films, and oriented films.

The term "gsm" refers herein to grams per square meter.

The term "hydrophilic" refers herein to fibers or the surfaces of fibers that are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams that attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers that can be continuous or discontinuous, are generally smaller than about 0.6 denier, and can be tacky and self-bonding when deposited onto a collecting surface.

The term "nonwoven" refers herein to materials and webs of material that are formed without the aid of a textile weaving or knitting process. The materials and webs of materials can have a structure of individual fibers, filaments, or threads (collectively referred to as "fibers") that can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials that are compliant and that will readily conform to the general shape and contours of the wearer's body.

The term "spunbond" refers herein to small diameter fibers that are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an aspect, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an aspect, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material that softens and that can be shaped when exposed to heat and that substantially returns to a non-softened condition when cooled.

The term "user" or "caregiver" refers herein to one who fits an absorbent article, such as, but not limited to, a diaper, training pant, youth pant, incontinent product, or other absorbent article about the wearer of one of these absorbent articles. A user, a wearer, and/or a caregiver can be the same person, depending on the situation.

Figure 2:
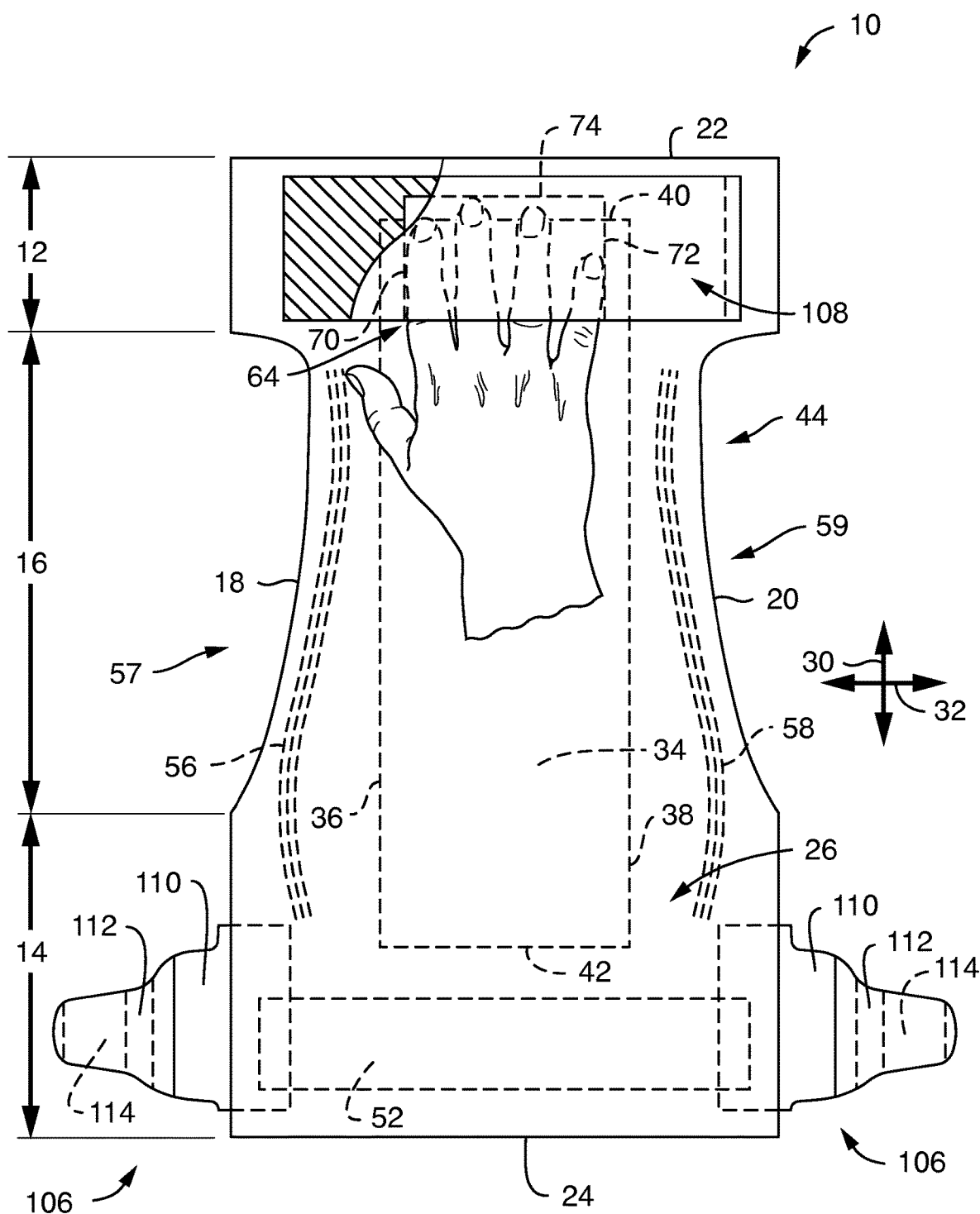
FIG. 2 is a top plan view of the absorbent article of FIG. 1 in a prior art aspect, illustrating a caregiver's fingers in a pocket.
Figure 3:
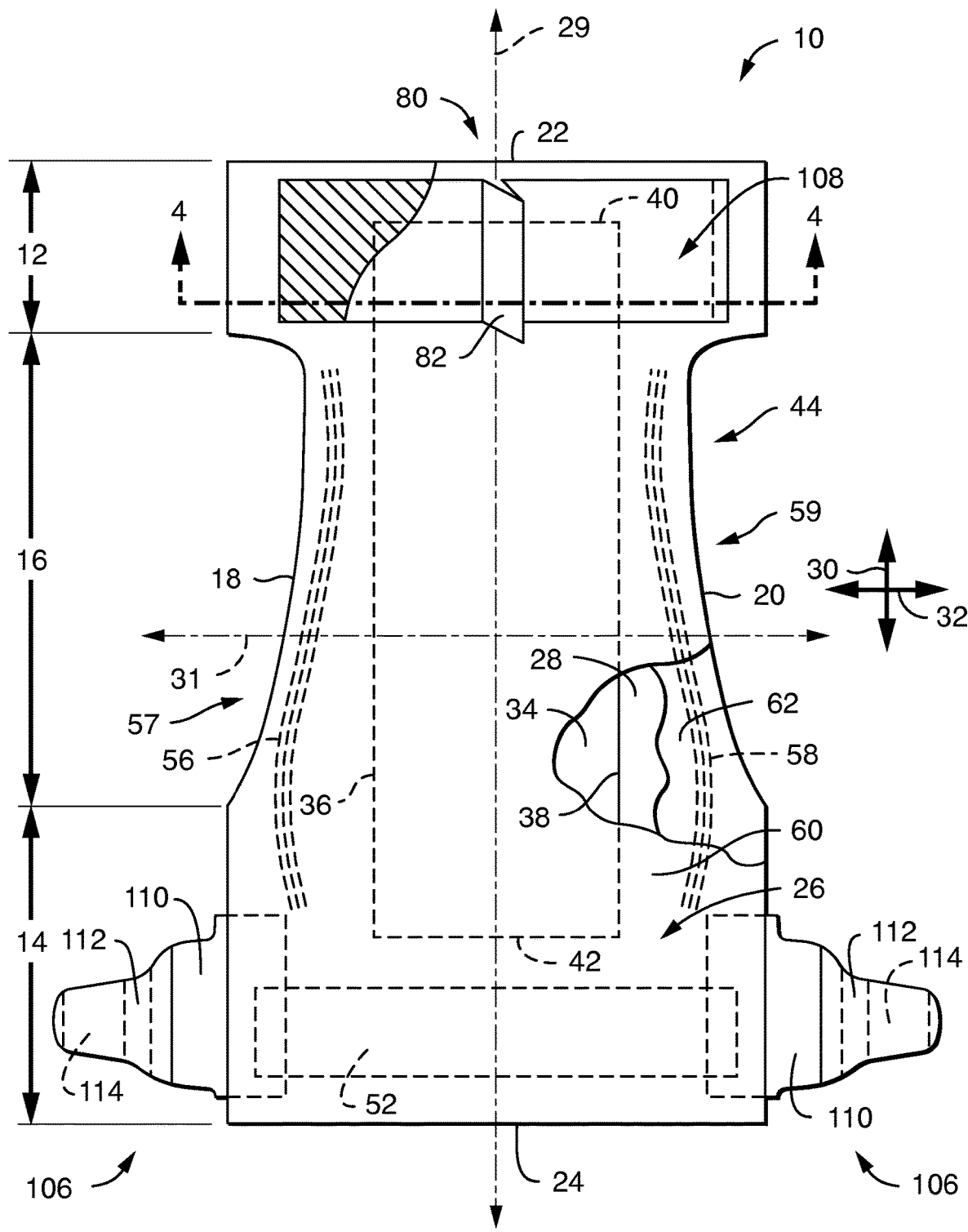
FIG. 3 is a top plan view of an exemplary aspect of an absorbent article, the absorbent article being in a stretched, laid flat configuration, with the outer cover facing the viewer, and with a gripper handle of the present disclosure.

Referring to FIGS. 1 and 2, a non-limiting illustration of an absorbent article 10, for example, a diaper, is illustrated. Other aspects of the absorbent article could include training pants, youth pants, adult incontinence garments, and feminine hygiene articles. While the aspects and illustrations described herein can generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The absorbent article 10 illustrated in FIGS. 1 and 2 includes a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. The absorbent article 10 has a pair of longitudinal side edges, 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 22 and 24, of the absorbent article 10 are configured to encircle the waist of the wearer and together define a central waist opening for the waist of the wearer. Portions of the longitudinal side edges, 18 and 20, in the crotch region 16 can generally define leg openings for the legs of the wearer when the absorbent article 10 is worn.

The absorbent article 10 can include an outer cover 26 and a bodyside liner 28, the bodyside liner 28 being depicted in the cut-away portion of FIG. 1. In an aspect, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated aspect, can coincide with the length and width of the absorbent article 10. As illustrated in FIG. 1, the absorbent article 10 can have a longitudinal axis 29 extending in the longitudinal direction 30 and a lateral axis 31 extending in the lateral direction 32.

An absorbent body 34 can be disposed between the outer cover 26 and the bodyside liner 28. The absorbent body 34 can have longitudinal edges, 36 and 38, which, in an aspect, can form portions of the longitudinal side edges, 18 and 20, respectively, of the absorbent article 10. The absorbent body 34 can have opposite first and second end edges, 40 and 42, respectively, which, in an aspect, can form portions of the waist edges, 22 and 24, respectively, of the absorbent article 10. The first end edge 40 can be in the front waist region 12. The second end edge 42 can be in the rear waist region 14. In an aspect, the absorbent body 34 can have a length and width that are the same as or less than the length and width of the absorbent article 10. The bodyside liner 28, the outer cover 26, and the absorbent body 34 can form part of an absorbent assembly 44. The absorbent assembly 44 can also include other components not shown herein, such as a fluid transfer layer and a fluid acquisition layer, as are known in the art.

The absorbent article 10 can be configured to contain and/or absorb liquid, solid, and semi-solid body exudates discharged from the wearer. For example, containment flaps (not shown), which are known in the art, can be configured to provide a barrier to the lateral flow of body exudates. To further enhance containment and/or absorption of body exudates, in some aspects the absorbent article 10 can suitably include a waist elastic member, such as a rear waist elastic member 52. In some aspects, the absorbent article 10 can include a front waist elastic member, although one is not depicted herein. The absorbent article 10 can further include leg elastic members, 56 and 58, as are known to those skilled in the art. The rear waist elastic member 52 can be attached to the outer cover 26 and/or the bodyside liner 28 along the rear waist edge 24 and can extend over part or all of the rear waist edge 24. In an aspect shown in FIGS. 1 and 2, the rear waist elastic member 52 is attached to the bodyside liner 28. The leg elastic members, 56 and 58, can be attached to the outer cover 26 and/or the bodyside liner 28 along the opposite longitudinal side edges, 18 and 20, and positioned in the crotch region 16 of the absorbent article 10. The leg elastic members, 56 and 58, can be curved as shown in FIGS. 1 and 2, or can be parallel to the longitudinal axis 29 as is known in the art.

The outer cover 26 and/or portions thereof can be breathable and/or liquid impermeable. The outer cover 26 and/or portions thereof can be elastic, stretchable, or non-stretchable. The outer cover 26 can be constructed of a single layer, multiple layers, laminates, spunbond fabrics, films, meltblown fabrics, elastic netting, microporous webs, bonded-carded webs or foams provided by elastomeric or polymeric materials. In an aspect, for example, the outer cover 26 can be constructed of a microporous polymeric film, such as polyethylene or polypropylene.

In an aspect, the outer cover 26 can be a single layer of a liquid impermeable material, such as a polymeric film. In an aspect, the outer cover 26 can be suitably stretchable, and more suitably elastic, in at least the lateral direction 32 of the absorbent article 10. In an aspect, the outer cover 26 can be stretchable, and more suitably elastic, in both the lateral 32 and the longitudinal 30 directions. In an aspect, the outer cover 26 can be a multi-layered laminate in which at least one of the layers is liquid impermeable. In an aspect, such as that shown in FIG. 1, the outer cover 26 can be a two layer construction, including an outer layer 60 material and an inner layer 62 material that can be bonded together such as by a laminate adhesive. Suitable laminate adhesives can be applied continuously or intermittently as beads, a spray, parallel swirls, or the like, but it is to be understood that the inner layer 62 can be bonded to the outer layer 60 by other bonding methods, including, but not limited to, ultrasonic bonds, thermal bonds, pressure bonds, or the like.

The outer layer 60 of the outer cover 26 can be any suitable material and can be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 60 of an outer cover 26 can be a 20 gsm spunbond polypropylene non-woven web. The outer layer 60 can also be constructed of the same materials from which the bodyside liner 28 can be constructed as described herein.

The liquid impermeable inner layer 62 of the outer cover 26 (or the liquid impermeable outer cover 26 where the outer cover 26 is of a single-layer construction) can be either vapor permeable (i.e., "breathable") or vapor impermeable. The liquid impermeable inner layer 62 (or the liquid impermeable outer cover 26 where the outer cover 26 is of a single-layer construction) can be manufactured from a thin plastic film. The liquid impermeable inner layer 62 (or the liquid impermeable outer cover 26 where the outer cover 26 is of a single-layer construction) can inhibit liquid body exudates from leaking out of the absorbent article 10 and wetting articles, such as bed sheets and clothing, as well as the wearer and caregiver.

Where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material that has been coated or otherwise treated to impart a desired level of liquid impermeability.

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. For example, FIGS. 1 and 2 illustrate an absorbent body 34 that is rectangular in shape, with a first end edge 40 and second end edge 42 that are parallel to one another and the lateral axis 31. The size and the absorbent capacity of the absorbent body 34 should be compatible with the size of the intended wearer (infants to adults) and the liquid loading imparted by the intended use of the absorbent article 10. The absorbent body 34 can have a length and width that can be less than or equal to the length and width of the absorbent article 10. The absorbent body 34 can have longitudinal side edges, 36 and 38, and front and back end edges, 40 and 42.

In an aspect, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an aspect, the absorbent body 34 can be a matrix of cellulosic fluff and superabsorbent material. In an aspect, the absorbent body 34 can be constructed of a single layer of materials, or in the alternative, can be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers that have been hydrophilized by suitable means. The fibers can be hydrophilized, for example, by treatment with a surfactant, treatment with silica, treatment with a material that has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an aspect, the absorbent body 34 can be free of superabsorbent material.

The absorbent body 34 can be superposed over the inner layer 62 of the outer cover 26 and can be bonded to the inner layer 62 of the outer cover 26, such as by being bonded thereto with adhesive. However, it is to be understood that the absorbent body 34 can be in contact with, and not bonded with, the outer cover 26 and remain within the scope of this disclosure. In an aspect, the outer cover 26 can be composed of a single layer and the absorbent body 34 can be in contact with the singer layer of the outer cover 26. In an aspect, a layer, such as but not limited to, a fluid transfer layer (not shown), can be positioned between the absorbent body 34 and the outer cover 26.

The bodyside liner 28 of the absorbent article 10 can overlay the absorbent body 34 and the outer cover 26 and can isolate the wearer's skin from liquid waste retained by the absorbent body 34. In various aspects, a fluid transfer layer (not shown) can be positioned between the bodyside liner 28 and the absorbent body 34. In various aspects, an acquisition layer (not shown) can be positioned between the bodyside liner 28 and the absorbent body 34 or a fluid transfer layer, if present. In various aspects, the bodyside liner 28 can be bonded to the acquisition layer, or to the fluid transfer layer if no acquisition layer is present, via adhesive and/or by a point fusion bonding. The point fusion bonding can be selected from ultrasonic, thermal, pressure bonding, and combinations thereof.

In an aspect, the bodyside liner 28 can extend beyond the absorbent body 34 and/or a fluid transfer layer, if present, and/or an acquisition layer, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. The bodyside liner 28 can be narrower than the outer cover 26, but it is to be understood that the bodyside liner 28 and the outer cover 26 can be of the same dimensions, or that the bodyside liner 28 can be of greater width than the outer cover 26. It is also contemplated that the bodyside liner 28 not extend beyond the absorbent body 34 and/or not be secured to the outer cover 26. It is further contemplated that the bodyside liner 28 can be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Patent Application Publication No. 2014/0121623 invented by Kirby, Scott S. C. et al. In a preferred aspect, the bodyside liner 28 includes a body-facing surface that provides an uneven surface at least in the front waist region 12, such as a body-facing surface that includes projections as disclosed in U.S. Patent Application Publication No. 2014/0121623 noted above. Such a bodyside liner provides additional benefits in softness and assists in cleaning the wearer's skin when the caregiver uses the absorbent article 10 to wipe the wearer.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an aspect, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, and end-to-end can be used without departing from the scope of this disclosure. In an aspect, a bodyside liner 28 can be a spunbond substrate with a basis weight from about 10 or 12 to about 15 or 20 gsm. In an aspect, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials that are generally non-elastomeric. In an aspect, the bodyside liner 28 can be stretchable, and more suitably elastic. In an aspect, the bodyside liner 28 can be suitably stretchable and more suitably elastic in at least the lateral or circumferential direction of the absorbent article 10. In other aspects, the bodyside liner 28 can be stretchable, and more suitably elastic, in both the lateral and the longitudinal directions 32, 30, respectively.

Leg elastic members 56, 58 (labeled in FIGS. 1 and 2) can be secured to the outer cover 26, such as by being bonded thereto by laminate adhesive, generally laterally inward of the longitudinal side edges, 18 and 20, of the absorbent article 10. The leg elastic members 56, 58 can form elasticized leg cuffs 57, 59, respectively, that further help to contain body exudates. In an aspect, the leg elastic members 56, 58 can be disposed between the inner layer 62 and outer layer 60 of the outer cover 26 or between other layers of the absorbent article 10. The leg elastic members 56, 58 can be a single elastic member, or each leg elastic member 56, 58 can include more than one elastic member, such as illustrated herein. A wide variety of elastic materials can be used for the leg elastic members 56, 58. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Of course, the leg elastic members 56, 58 can be omitted from the absorbent article 10 without departing from the scope of this disclosure.

In an aspect, the absorbent article 10 can have one or more waist elastic members, such as rear waist elastic member 52, which can be formed of any suitable elastic material. The rear waist elastic member 52 can be in a rear waist region 14 of the absorbent article 10. Suitable elastic materials for waist elastic members can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic member 52 can be omitted from the absorbent article 10 without departing from the scope of this disclosure.

In an aspect, the absorbent article 10 can include a fastener system. The fastener system can include one or more back fasteners 106 and one or more front fasteners 108, with only one front fastener 108 being shown in FIGS. 1 and 2. Portions of the fastener system can be included in the front waist region 12, rear waist region 14, or both. The front fastener(s) 108 can be made from any suitable material. In an alternative aspect, the front fastener 108 can be the garment facing surface 27 of the outer cover 26.

The fastener system can be configured to secure the absorbent article 10 about the waist of the wearer and maintain the absorbent article 10 in place during use. In an aspect, the back fasteners 106 can include one or more materials bonded together to form a composite ear as is known in the art. For example, the composite fastener can be composed of a stretch component 110, a nonwoven carrier or hook base 112, and a fastening component 114.

Aspects of prior attempts to accommodate using the absorbent article 10 to wipe are illustrated in FIG. 2. A front fastener 108 is attached to the outer cover of the front waist region of the absorbent article 10. The front fastener, however, is attached to the outer cover on only three of four sides, i.e., along an upper lateral edge 74 and two side edges 70 and 72, allowing the front fastener 108 to act as a pocket 64. A caregiver can insert a hand in the pocket 64 to provide control of the absorbent article 10 and protection of the caregivers hand from BM contamination. This solution does add a significant amount of process complexity in that the front fastener laminating adhesive needs to be registered to create the pocket 64. In addition, in this execution there is no visual cue to the existence of the pocket 64 unless additional components are added to the pocket 64 to make it open in at least a post-wear configuration to cue the caregiver to its existence. Adding these additional components adds to the complexity of manufacture.

The present disclosure describes a gripper handle 80 positioned on the front central portion of the absorbent article 10 in the front waist region 12. The gripper handle 80 projects outwardly from the outermost surface of the absorbent article 10 (although the gripper handle 80 can also fold flat against the outermost surface during use of the absorbent article 10) for control of the absorbent article 10 during cleanup of BM and other exudates. Such a gripper handle 80 provides a visual cue for the caregiver.

The open nature of the gripper handle 80 allows a caregiver's hand to grip the handle to assist with an initial wiping of the skin of the wearer after the absorbent article 10 becomes soiled with exudates prior to disposing of the soiled absorbent article 10 and cleansing the wearer's skin.

Figure 6:
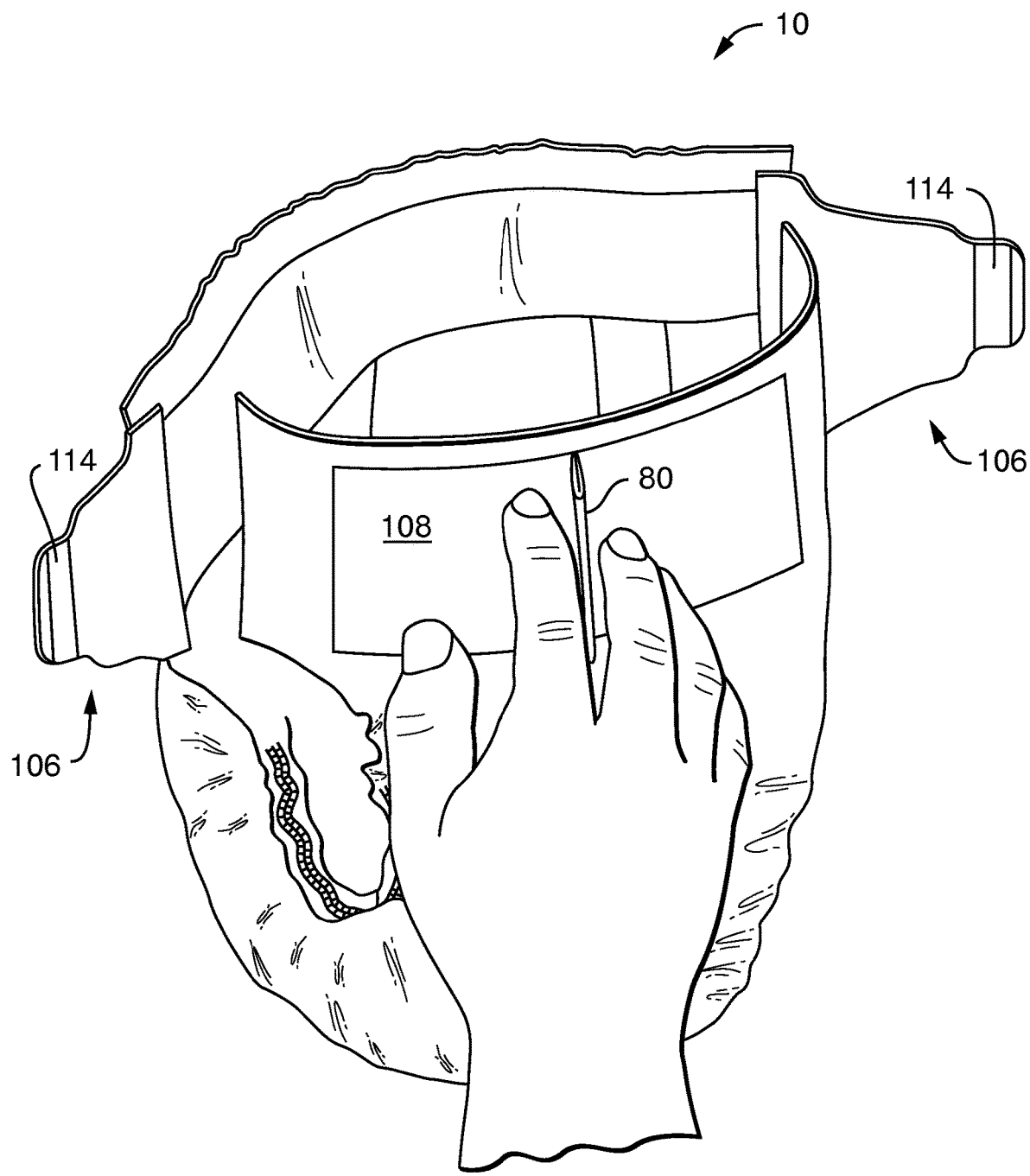
FIG. 6 is a perspective view of an absorbent article and a caregiver's hand gripping a gripper handle of the present disclosure.

In a more specific example, and as illustrated in FIGS. 3-6, a gripper handle 80 in the form of a folded fin is formed from the front fastener 108. The folded gripper fin 82 is formed by folding and bonding a portion of the front fastener 108. The folded gripper fin 82 is positioned in the lateral central region of the front fastener 108 and therefore in the front waist region 12. FIGS. 4 and 5 illustrate a cross-sectional view of the folded and bonded gripper fin 82. In other aspects more than one folded gripper fin 82 can be provided. The presence of the folded gripper fin 82 provides a visual cue to a caregiver that the folded gripper fin 82 can be used as a handle to grip the front waist region 12 of the absorbent article 10 for cleanup, as illustrated in FIG. 6. This solution provides a simpler process involving continuous gluing and a simple fold.

Figure 7:
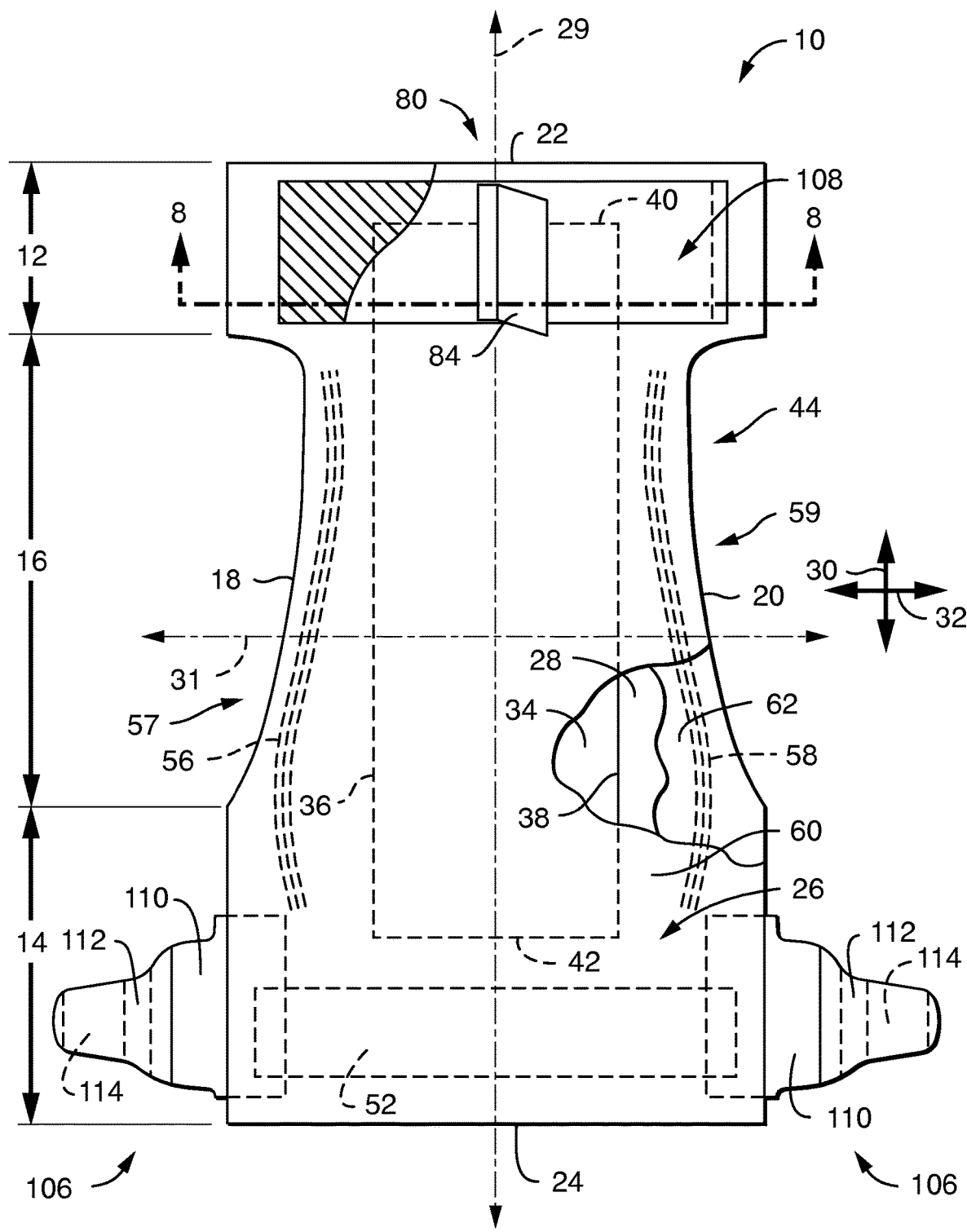
FIG. 7 is a top plan view of an exemplary aspect of an absorbent article, the absorbent article being in a stretched, laid flat configuration, with the outer cover facing the viewer, and with a gripper handle of the present disclosure.

In another aspect of the present disclosure, and as illustrated in FIGS. 6-9, a gripper handle 80 in the form of a bonded fin is attached to the outermost surface of the absorbent article 10, typically to the front fastener 108 or the outer cover 26. The bonded gripper fin 84 is formed separately and then bonded to the outermost surface of the absorbent article 10. The bonded gripper fin 84 is positioned in the lateral central region of the front waist region 12, as illustrated in FIG. 7. FIGS. 8 and 9 illustrate a cross-sectional view of the bonded gripper fin 84. In other aspects more than one bonded gripper fin 84 can be provided, or a combination of folded grippers fins 82 and bonded gripper fins 84 can be provided. The presence of the bonded gripper fin 84 provides a visual cue to a caregiver that the bonded gripper fin 84 can be used as a handle to grip the front waist region 12 of the absorbent article 10 for cleanup, as illustrated in FIG. 6. The caregiver can grip the handle between thumb and index finger, between index finger and middle finger, or in any other comfortable and suitable manner. This solution provides a simpler process involving continuous gluing. In one potential drawback, however, the solutions employing gripper fins 84 alone might not provide an adequate means for protecting the caregiver from BM contamination. The gripper fins 84 in any of these aspects can be made from a material that a back fastener 106 can releasably attach to.

Figure 10:
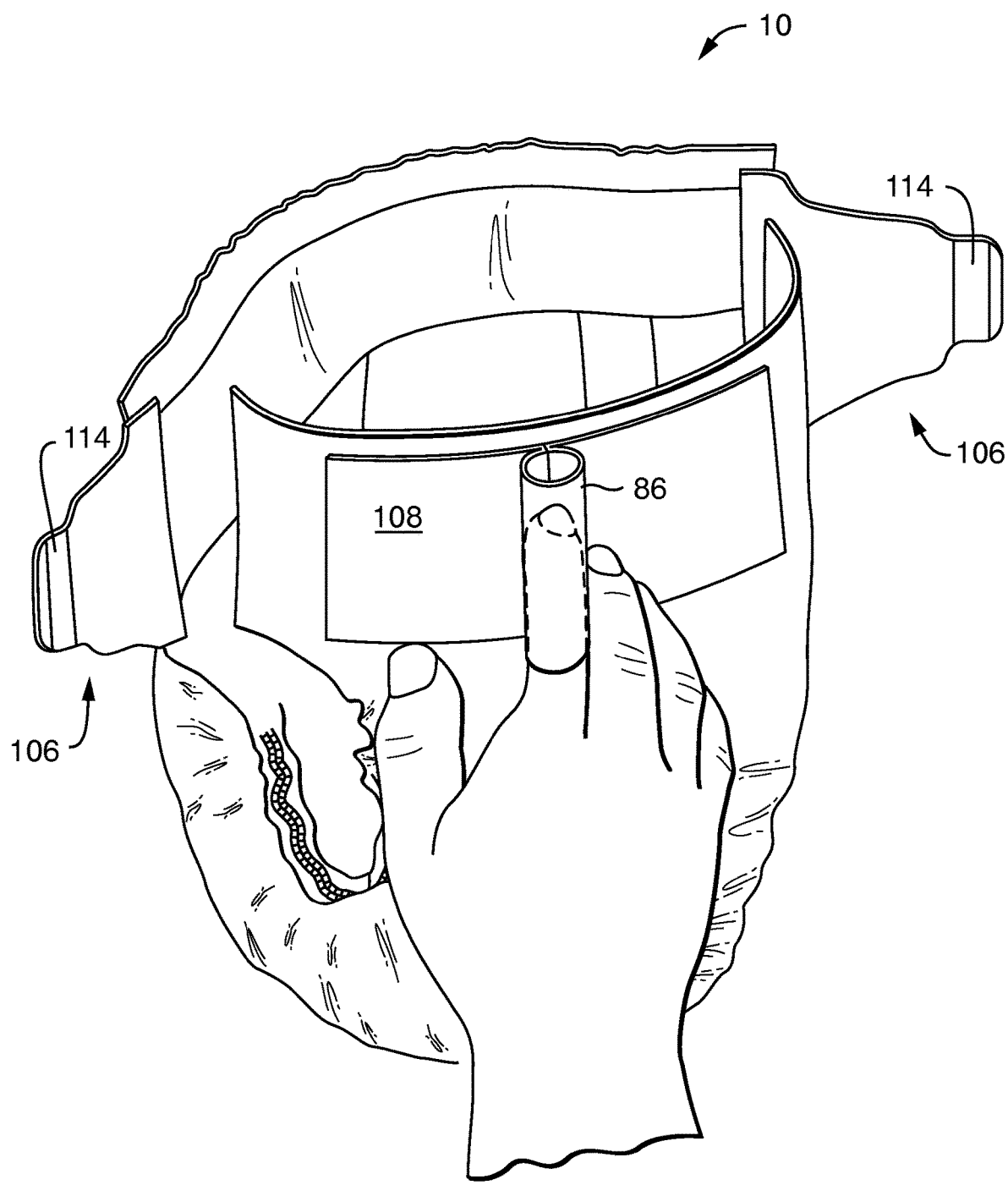
FIG. 10 is a perspective view of an absorbent article and a caregiver's hand gripping a gripper handle of the present disclosure.
Figure 11:
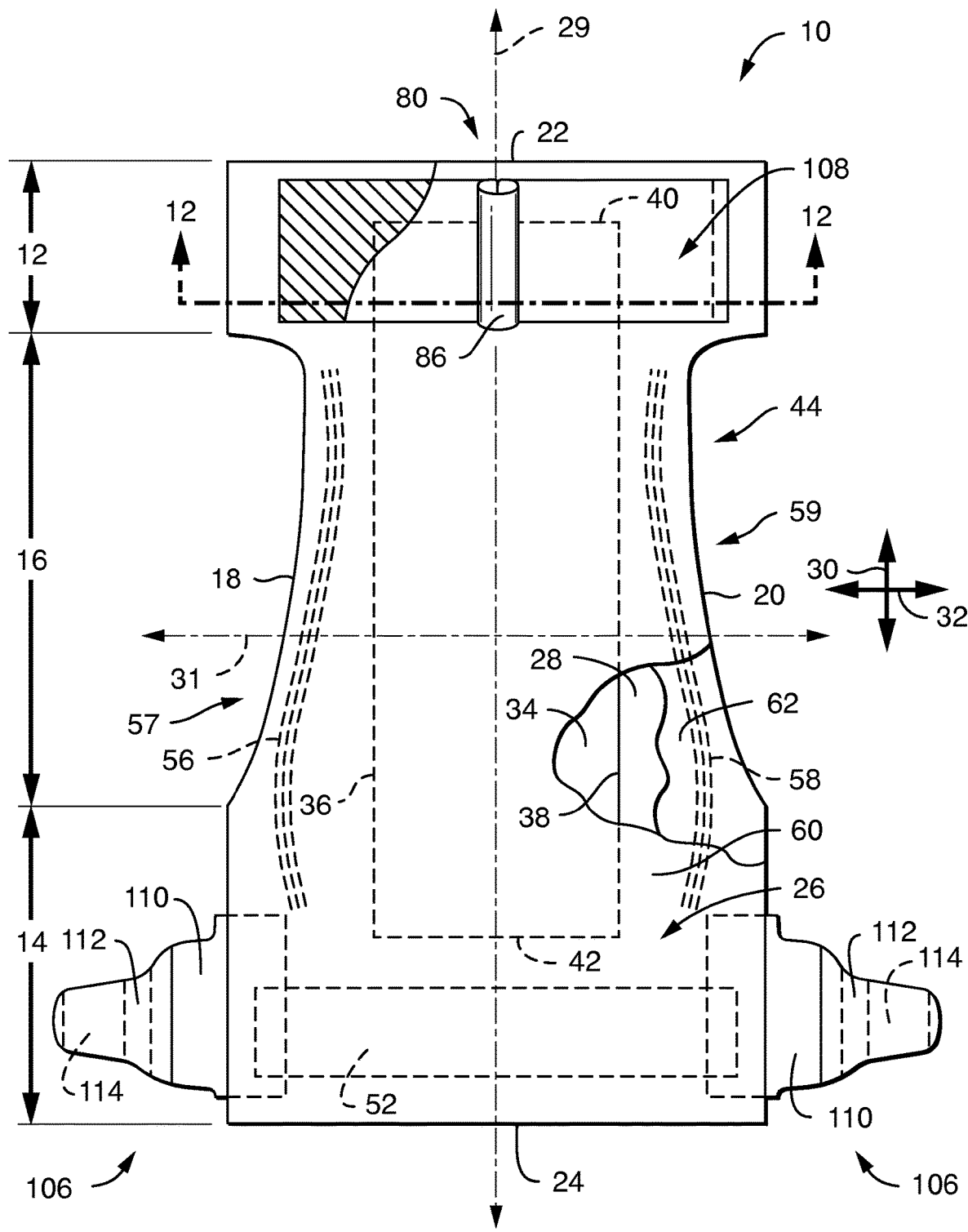
FIG. 11 is a top plan view of an exemplary aspect of an absorbent article, the absorbent article being in a stretched, laid flat configuration, with the outer cover facing the viewer, and with a gripper handle of the present disclosure.
Figure 12:
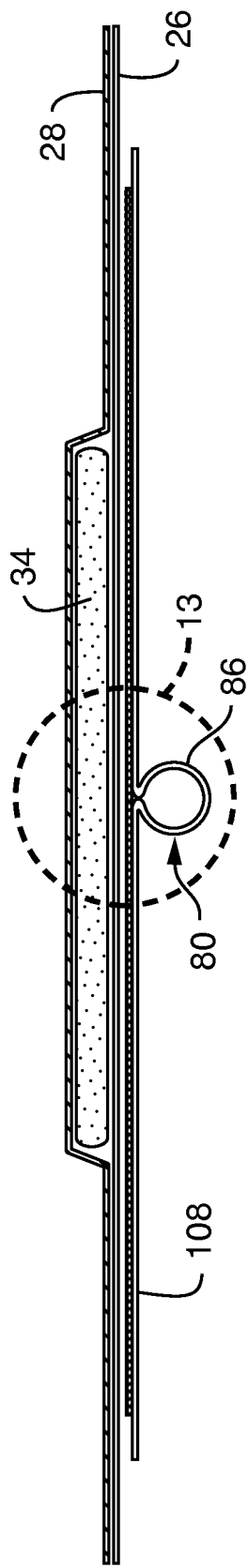
FIG. 12 is a cross-section view of the article of FIG. 11, taken along the 12-12 line of FIG. 11.
Figure 13:
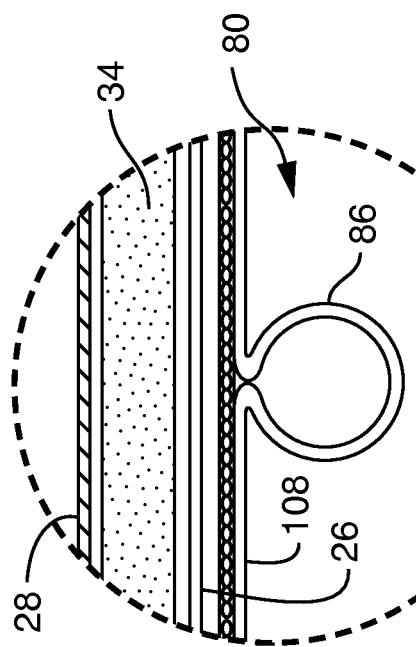
FIG. 13 is a close-up cross-section view of the article of FIG. 12.

In various other aspects of the present disclosure, and as illustrated in FIGS. 10-13, a gripper handle 80 in the form of a folded tube is formed from the front fastener 108. The folded gripper tube 86 is formed by folding and bonding a portion of the front fastener 108. The folded gripper tube 86 is positioned in the lateral central region of the front fastener 108 and therefore in the front waist region 12, as illustrated in FIG. 11. FIGS. 12 and 13 illustrate a cross-sectional view of the folded and bonded gripper tube 86. In other aspects more than one folded gripper tube 86 can be provided. The presence of the folded gripper tube 86 provides a visual cue to a caregiver that the folded gripper tube 86 can be used as a handle by inserting a finger to grip the front waist region 12 of the absorbent article 10 for cleanup, as illustrated in FIG. 10. The folded gripper tube 86 can be used as a miniature pocket for a finger as illustrated in FIG. 10, or the folded gripper tube 86 can be flattened and gripped in the manner illustrated in FIG. 6. It should be noted that the folded gripper tube 86 will likely appear as illustrated during manufacture and during use, but may be flattened when the absorbent article 10 is packaged. The caregiver simply needs to lift the folded gripper tube 86 away from the outer surface of the absorbent article 10 and insert a finger. In addition, the folded gripper tube 86 prevents the hand from sliding forward during BM cleanup, which helps to prevent BM contamination. This solution provides a simpler process involving continuous gluing and a simple fold.

Figure 14:
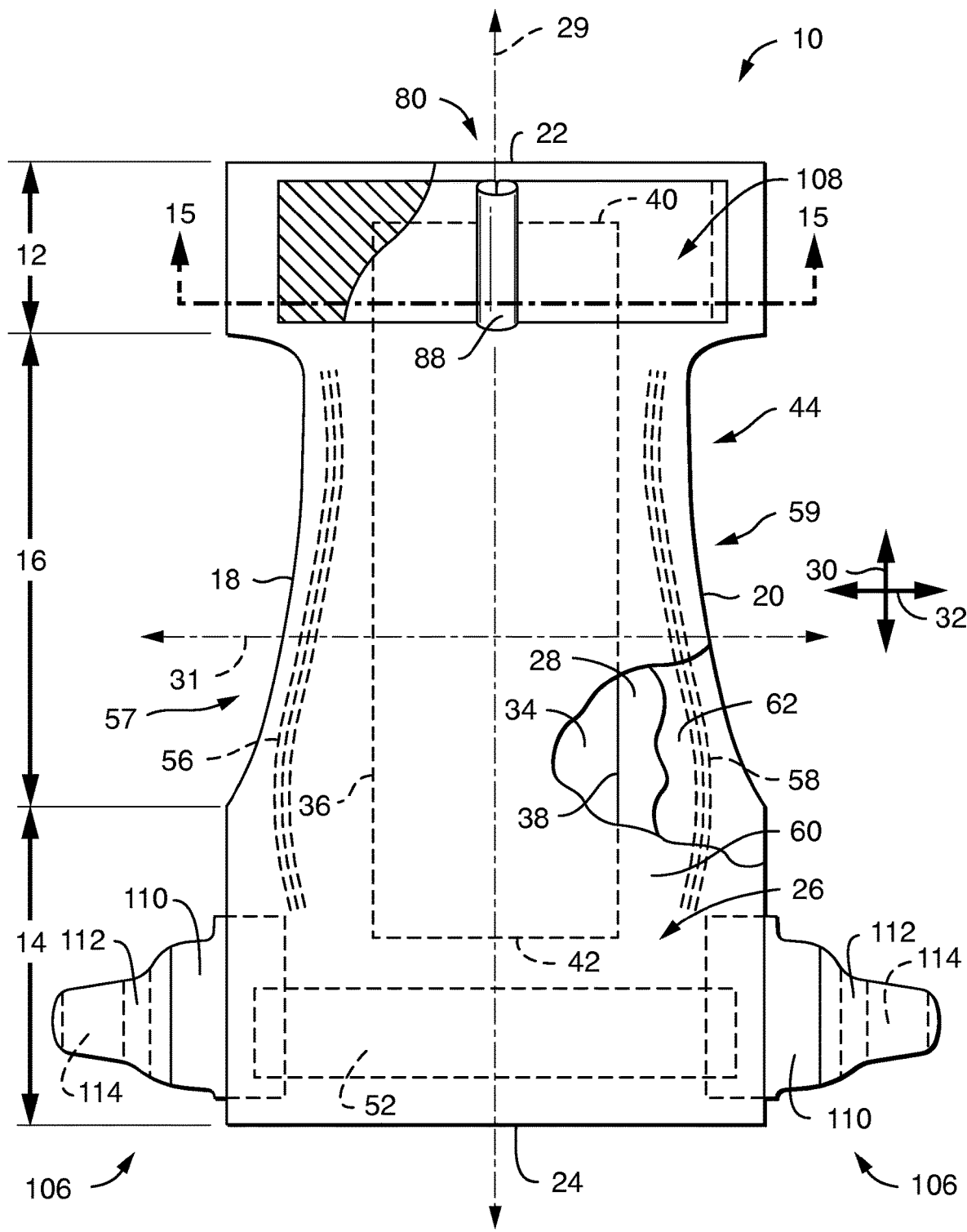
FIG. 14 is a top plan view of an exemplary aspect of an absorbent article, the absorbent article being in a stretched, laid flat configuration, with the outer cover facing the viewer, and with a gripper handle of the present disclosure.

In yet another aspect of the present disclosure, and as illustrated in FIGS. 10 and 14-16, a gripper handle 80 in the form of a bonded tube is attached to the outermost surface of the absorbent article 10, typically to the front fastener 108 or the outer cover 26. The bonded gripper tube 88 is formed separately and then bonded to the outermost surface of the absorbent article 10. The bonded gripper tube 88 is positioned in the lateral central region of the front waist region 12, as illustrated in FIG. 14. FIGS. 15 and 16 illustrate a cross-sectional view of the bonded gripper tube 88. In other aspects more than one bonded gripper tube 88 can be provided, or a combination of folded grippers tubes 86 and bonded gripper tubes 88 can be provided. The presence of the bonded gripper tube 88 provides a visual cue to a caregiver that the bonded gripper tube 88 can be used as a handle by inserting a finger to grip the front waist region 12 of the absorbent article 10 for cleanup, as illustrated in FIG. 10. The bonded gripper tube 88 can be used as a miniature pocket for a finger as illustrated in FIG. 10, or the bonded gripper tube 88 can be flattened and gripped in the manner illustrated in FIG. 6. It should be noted that the folded gripper tube 86 will likely appear as illustrated during manufacture and during use, but may be flattened when the absorbent article 10 is packaged. The caregiver simply needs to lift the folded gripper tube 86 away from the outer surface of the absorbent article 10 and insert a finger. In addition, the bonded gripper tube 88 prevents the hand from sliding forward during BM cleanup, which helps to prevent BM contamination. This solution provides a simpler process involving continuous gluing. The gripper tubes 86, 88 in any of these aspects can be made from a material that a back fastener 106 can releasably attach to.

In a first particular aspect, an absorbent article includes a front waist region, a rear waist region, and a crotch region, the front waist region having a front fastener and an outermost surface, the absorbent article further including a longitudinal axis and a lateral axis. The absorbent article also includes an absorbent assembly including a bodyside liner, an outer cover, and an absorbent body disposed between the bodyside liner and the outer cover; and a gripper handle disposed in the front waist region and extending from the outermost surface, wherein the outermost surface is one of the outer cover and the front fastener.

A second particular aspect includes aspect 1, wherein the gripper handle is affixed to the outermost surface.

A third particular aspect includes one or more of aspects 1 and 2, wherein the gripper handle is formed as part of the outermost surface.

A fourth particular aspect includes one or more of aspects 1-3, wherein the gripper handle is planar.

A fifth particular aspect includes one or more of aspects 1-4, wherein the gripper handle is a tab.

A sixth particular aspect includes one or more of aspects 1-5, wherein the gripper handle is a tube.

A seventh particular aspect includes one or more of aspects 1-6, wherein the tube is sized to accommodate a human finger.

An eighth particular aspect includes one or more of aspects 1-7, wherein the outermost surface is the outer cover.

A ninth particular aspect includes one or more of aspects 1-8, wherein the front fastener is the outermost surface.

A tenth particular aspect includes one or more of aspects 1-9, wherein the absorbent article includes a back fastener, and wherein the gripper handle is configured to engage with the back fastener.

An eleventh particular aspect includes one or more of aspects 1-10, wherein the gripper handle has a handle longitudinal axis, and wherein the handle longitudinal axis is generally parallel to the longitudinal axis of the absorbent article.

In a twelfth particular aspect, an absorbent article includes a front waist region, a rear waist region, and a crotch region, the front waist region having a front fastener and an outermost surface, the absorbent article further including a longitudinal axis and a lateral axis. The absorbent article also includes an absorbent assembly including a bodyside liner, an outer cover, and an absorbent body disposed between the bodyside liner and the outer cover; and a gripper handle disposed in the front waist region and extending from the outermost surface, wherein the gripper handle is affixed to the outermost surface, wherein the outermost surface is one of the outer cover and the front fastener, wherein the gripper handle has a handle longitudinal axis, and wherein the handle longitudinal axis is generally parallel to the longitudinal axis of the absorbent article.

A thirteenth particular aspect includes aspect 12, wherein the gripper handle is a tab.

A fourteenth particular aspect includes one or more of aspects 12 and 13, wherein the gripper handle is a tube.

A fifteenth particular aspect includes one or more of aspects 12-14, wherein the front fastener is the outermost surface.

A sixteenth particular aspect includes one or more of aspects 12-15, wherein the absorbent article includes a back fastener, and wherein the gripper handle is configured to engage with the back fastener.

In a seventeenth particular aspect, an absorbent article includes a front waist region, a rear waist region, and a crotch region, the front waist region having a front fastener and an outermost surface, the absorbent article further including a longitudinal axis and a lateral axis. The absorbent article also includes an absorbent assembly including a bodyside liner, an outer cover, and an absorbent body disposed between the bodyside liner and the outer cover; and a gripper handle disposed in the front waist region and extending from the outermost surface, wherein the gripper handle is formed as part of the outermost surface, wherein the outermost surface is one of the outer cover and the front fastener, wherein the gripper handle has a handle longitudinal axis, and wherein the handle longitudinal axis is generally parallel to the longitudinal axis of the absorbent article.

An eighteenth particular aspect includes aspect 17, wherein the gripper handle is a tab.

A nineteenth particular aspect includes one or more of aspects 17 and 18, wherein the gripper handle is a tube.

A twentieth particular aspect includes one or more of aspects 17-19, wherein the front fastener is the outermost surface.

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by references, the meaning or definition assigned to the term in this written document shall govern.

While particular aspects of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. An absorbent article including a front waist region including a front waist edge, a rear waist region, and a crotch region, the absorbent article further including a longitudinal axis and a lateral axis, the absorbent article comprising:
    an absorbent assembly including a bodyside liner, an outer cover, and an absorbent body disposed between the bodyside liner and the outer cover; and
    a front fastener disposed on the outer cover and forming an outermost surface of the article;
    a pair of back fasteners disposed proximate the rear waist region, the pair of back fasteners configured to releasably attach with the front fastener; and
    a tab bonded to and projecting away from the front fastener, wherein the tab has a tab handle longitudinal axis, and wherein the tab handle longitudinal axis is generally parallel to the longitudinal axis of the absorbent article.

2. The absorbent article of claim 1, wherein the tab has a tube shape.

3. An absorbent article including a front waist region including a front waist edge, a rear waist region, and a crotch region, the absorbent article further including a longitudinal axis and a lateral axis, the absorbent article comprising:
    an absorbent assembly including a bodyside liner, an outer cover, and an absorbent body disposed between the bodyside liner and the outer cover; and
    a front fastener disposed on the outer cover and forming an outermost surface of the article, the front fastener comprising a laterally extending top edge disposed proximate the front waist edge and a laterally extending bottom edge disposed distal the front waist edge, a portion of the front fastener extending between and including both of the laterally extending top edge and the laterally extending bottom edge being un-connected from and projecting away from the outer cover to form a tab; and
    a pair of back fasteners disposed proximate the rear waist region, the pair of back fasteners configured to releasably attach with the front fastener.

4. The absorbent article of claim 3, wherein the tab has a tube shape.

5. The absorbent article of claim 3, wherein the portion the front fastener un-connected from the outer cover is bonded to itself.

6. The absorbent article of claim 1, wherein the tab comprises a laterally extending top edge disposed proximate the front waist edge, a laterally extending bottom edge disposed proximate distal the front waist edge, and a pair of opposing longitudinally extending side edges, wherein one of the longitudinally extending side edges is not bonded to the front fastener.

7. The absorbent article of claim 6, wherein a portion of each of the laterally extending top edge and the laterally extending bottom edge are not bonded to the front fastener.

8. The absorbent article of claim 7, wherein the un-bonded portions of the laterally extending top edge, the laterally extending bottom edge, and the one of the longitudinally extending side edges form a continuous un-bonded edge.

9. The absorbent article of claim 1, wherein the tab is bonded to the front fastener along a bond, and wherein the bond intersects with the absorbent article longitudinal axis.

* * * * *